(12) United States Patent
Kareem

(10) Patent No.: US 7,695,744 B1
(45) Date of Patent: Apr. 13, 2010

(54) NATURAL SUPPLEMENT OF CHOLESTEROL LOWERING OIL SEEDS AND NUTS AND METHOD OF MANUFACTURE

(76) Inventor: M. Zubair Kareem, 12 Spring Meadows, South Hadley, MA (US) 01075

( * ) Notice: Subject to any disclaimer, the term of this patent is extended or adjusted under 35 U.S.C. 154(b) by 661 days.

(21) Appl. No.: 11/560,429

(22) Filed: Nov. 16, 2006

Related U.S. Application Data

(60) Provisional application No. 60/597,192, filed on Nov. 16, 2005.

(51) Int. Cl.
*A23L 1/36* (2006.01)
*A61K 36/52* (2006.01)
*A61K 36/55* (2006.01)
*A61K 36/28* (2006.01)

(52) U.S. Cl. .................. 424/776; 424/771; 424/768; 424/764; 424/758; 424/725; 426/44

(58) Field of Classification Search .................. None
See application file for complete search history.

(56) References Cited

U.S. PATENT DOCUMENTS

| | | | | |
|---|---|---|---|---|
| 4,931,304 | A | * | 6/1990 | Sharma .................. 426/632 |
| 5,612,074 | A | * | 3/1997 | Leach .................... 426/74 |
| 5,843,499 | A | | 12/1998 | Moreau et al. |
| 5,855,892 | A | | 1/1999 | Potter et al. |
| 5,910,317 | A | | 6/1999 | Broaddus |
| 6,641,847 | B1 | | 11/2003 | Nawar |
| 6,787,151 | B2 | | 9/2004 | Meijer et al. |
| 6,787,162 | B1 | | 9/2004 | Bonilla |
| 2003/0077336 | A1 | | 4/2003 | Maffetone |
| 2003/0235595 | A1 | | 12/2003 | Chen et al. |
| 2004/0253327 | A1 | | 12/2004 | Niazi et al. |
| 2005/0089592 | A1 | | 4/2005 | Chevaux et al. |
| 2005/0214346 | A1 | | 9/2005 | Bringe et al. |

FOREIGN PATENT DOCUMENTS

WO  WO/2004/066938 A2   8/2004

OTHER PUBLICATIONS

Hu, et. al, "Nut Consumption and Risk of Coronary Heart Disease: A Review of Epidemiologic Evidence", Harvard School of Public Health, Current Sciences Inc. 1999 I : 204-209.
Lovejoy, et al,"Effect of Diets Enriched in Almonds on Insulin Action and Serum Lipids in Adults with Normal Glucose Tolerance of Type 2 Diabetes", Am J. Clin Nutr. 2002;1000-6.
Jenkins, et al, "Dose Response of Almonds on Coronary Heart Disease Risk Factors . . . ", Journ. of American Heart Association 2002; 106; 1327-1332.
Jambazian, et al, "Almonds in the Diet Simultaneously Improve Plasma α-Tocopherol Concentrations and Reduce Plasma Lipids"; Journ. of Am. Dietetic Assoc. 2005,105:449-454.
Lucas, et al, "Flaxseed Reduces Plasma Cholesterol and Atherosclerotic Lesion Formation in Ovariectomized Golden Syrian Hamsters", Elsevier, Ireland 2004, 223-229.
Gonthier, et al, "Feeding Micronized and Extruded Flaxseed to Dairy Cows.."; Am. Dairy Science Assoc. 2005, J. Dairy Sci. 88:748-756.
Ingram, et al, "Effects of Flaxseed and Flax Oil Diets in a Rat-5/6 Renal Ablation Model"; Am Journ. of Kidney Diseases, vol. 25, No. 2, 1995: 320-329.
Wiesenfeld, et al, "Flaxseed Increased αlinolenic and Eicosapentaenoic Acid and Decreased Arachidonic Acid . . . "Food and Chem. Toxiocology 41 (2003), 841-855.
Scheideler, et al, "The Combined Influence of Dietary Flaxseed Variety, Level, Form, and Storage Conditions on Egg Prod. . . . "; Dept. Animal Sci., 1996 Poultry Sci. 75:1221-6.
Stuglin, et al, "Effect of Flaxseed Consumption on Blood Pressure . . . ", Depts. of Physiolgy & Cardiology, Uni.of Saskatchewan, Canada, 2005 , J. Cardiovasc. Pharmocol 23-27.

\* cited by examiner

*Primary Examiner*—Patricia Leith
(74) *Attorney, Agent, or Firm*—Deborah A. Basile; Karen K. Chadwell

(57) ABSTRACT

A specially formulated oil seed and nut based natural product composition useful in lowering total serum cholesterol and low density lipoprotein levels and increasing high density lipoprotein levels in humans. The composition is preferably formed by heating a variety of types of oil seeds and nuts at a predetermined temperature and for a predetermined period of time, categorizing the individual types of seeds and nuts into individual sets, grinding the seeds and nuts in each set into a meal, and combining the meals from each set to form a single composition.

5 Claims, No Drawings

NATURAL SUPPLEMENT OF CHOLESTEROL LOWERING OIL SEEDS AND NUTS AND METHOD OF MANUFACTURE

CROSS REFERENCE TO RELATED APPLICATIONS

This application claims the benefit of U.S. Provisional Application No. 60/597,192 filed on Nov. 16, 2005.

BACKGROUND OF THE INVENTION

1. Field of Invention

The present invention relates generally to the maintenance of health and specifically to the lowering of systemic cholesterol levels in humans through the regular administration of a composition comprising oil seeds and nuts.

2. Background of the Invention

Certain abnormalities relative to cholesterol levels (e.g., high total cholesterol levels or high levels of low density lipoprotein ("LDL"), and/or low levels of high density lipoprotein ("HDL")) are defined risk factors for cardiovascular, cerebrovascular, and peripheral vascular disease. Correction of these abnormalities decreases the risk of heart disease and stroke. Correction may be possible with dietary modifications but many times a medicine is needed. Presently available medicines are effective but they also carry the risk of sometimes significant side effects. Accordingly, in spite of the widespread incidence of cholesterol abnormalities, large numbers of people with these abnormalities do not take medicines.

Many studies have indicated that the consumption of many individual nuts and oil seeds are useful to correct cholesterol abnormalities. Nuts and oil seeds contain a variety of fats. Research has suggested that nuts and oil seed consumption in animals and humans has a beneficial effect for prevention of vascular or coronary artery disease. Five large prospective cohort studies (The Adventist Health Study, the Iowa Women Health Study, the Nurses' Health Study, the Physicians' Health Study, and the CARE Study) have all found an inverse relationship between nut consumption and risk of coronary heart disease. Hu and Stampfer, in their review of this subject, suggested that nuts should assume a more prominent place in the U.S. Department of Agriculture Food Guide Pyramid.

Many studies are available reporting the effect of an individual variety of nut. For example, Lovejoy et al. studied the effect of diets enriched in almonds on insulin action and serum lipids in normal adults and with type-2 diabetes. A beneficial effect was noted on serum lipids and the diet did not alter insulin sensitivity in healthy adults or glycemia in individuals with diabetes. Jenkins et al. studied the effect of almonds as a snack in hyperlipidemic subjects. A beneficial effect to lower LDL was noted in a dose response manner without any overt effects. Jambazian et al. reported improved plasma alpha-tocopherol concentrations and reduced plasma lipids in human subjects given an almond supplemented diet.

Additionally, flaxseed is a rich source of lignans, alpha-linolenic acid and soluble fiber mucilage. The effect of flaxseed was studied by Lucas et al. in ovariectomized Golden Syrian hamsters (an animal model with significantly elevated plasma lipids). Flaxseed consumption reduced the aortic fatty streak area and the incidence of lesions to levels similar to the sham group. Further studying the affects of flaxseed, Gonthier et al. studied the changes in milk fatty acid composition in dairy cows fed with flaxseed. It was concluded that feeding raw or heated flaxseed to dairy cows altered the blood and milk fatty acid composition and feeding extruded flaxseed relative to raw or micronized flaxseed had a negative effect on milk yield and milk composition. Ingram et al. studied the effects of flaxseed and flax oil in a rat renal ablation model. Rats fed with flaxseed or flaxseed oil had slowed decline in renal function, and a favorable effect on blood pressure and plasma lipids.

Defatted flaxseed meal and flaxseed consumption and their effects were studied in rats by Wiesenfeld et al. Flaxseed more than defatted flaxseed meal altered fatty acid profiles. Defatted flaxseed and a 40% flaxseed diet significantly reduced serum cholesterol. They also found a reduction of liver vitamin E in rats fed a diet consisting of 40% flaxseed.

Little is known about the effect of flaxseed type, brown versus golden. Scheideler et al. studied the effects of flaxseed variety, level, form and storage conditions on egg production and composition among hens. Supplementation of flaxseed significantly increased percentage white and decreased yolk compared to control but had no effects on egg cholesterol. Flaxseed additionally decreased feed consumption, weight gain, and egg whites. The level of linolenic acid (C18:3n-3) into eggs increased linearly as the level of dietary flaxseed increased.

Stuglin and Prasad studied the effects of flaxseed consumption on serum lipids, hemopoitic system and liver and kidney function in healthy human volunteers. Daily ingestion of 32.7 grams ("g") of flaxseed administered over a four week period of time did not have a deleterious effect on the hemopoitic system, or on the renal or hepatic system. The level of serum triglyceride was elevated.

Lucas et al. also studied the effect of flaxseed on biomarkers of bone metabolism in postmenopausal women. They did not find a benefit in that regard but flaxseed consumption was shown to improve lipid profiles (lowering of total cholesterol and non HDL lipoprotein cholesterol by 6%.)

Bierenbaum et al. studied the effect of flaxseed containing bread and ground flaxseed in 15 hyperlipemic human subjects. Serum total and LDL cholesterol levels were reduced significantly, while HDL cholesterol did not change. Also, thrombin-stimulated platelet aggregation decreased with supplement.

With regards to nuts, multiple studies are available describing the effect of a walnut containing diet on humans. For example, Abbey et al., in 1994, reported significant reduction of total and LDL cholesterol in male volunteers taking diet with almonds or walnuts. In 2000, Zambon et al. reported that substituting walnuts for monounsaturated fat improves the serum lipid profile of hyhpercholesterolemic men and women and the diet was well tolerated. The effect of walnut consumption in combined hyperlipidemia was reported by Almario et al., in 2001. Walnut supplementation beneficially altered the lipid distribution of the lipoprotein subclasses. In 2002, Feldman reviewed the scientific evidence for a beneficial health relationship between walnuts and coronary heart disease and confirmed these findings. Similar results were reported by Iwamoto et al. with Japanese male and female subjects. They also reported that the most prominent change was the elevation of alpha-linolenic acid that might be responsible for the lowering of LDL. The effect of walnut consumption was studied in subjects with borderline high total cholesterol by Morgan et al., in 2002, and in subjects with type-2 diabetes by Tapsell et al., in 2004. Theses studies revealed similar results: high HDL and low LDL without any significant change in body weight or glucose levels as based on a hemoglobin A1c ("HgA1c") test. Ros et al., in 2004, reported that an increased consumption of walnuts improved endothelial function in hypercholesterolemic subjects.

Poppy seeds have a distinct set of sterols as described by Johansson. The nutritional value of poppy seed oil relative to other oils was studied in rats by Beare-Rogers et al. and the noted effects were similar to olive oil. Not much is currently known about the effect of poppy seeds on lipid level in humans.

Sesame seed on the other hand has been shown, by Yamashita et al., to increase vitamin E concentration in rats. Additionally, in 2001 Cooney et al. reported that sesame seed consumption has beneficial effects on plasma tocophorol, the major vitamers of vitamin E. This effect was not seen with consumption of walnuts or soy oil.

Liapkov in 1978 studied the effect of sunflower seed supplemented feed to rats. Liapkov reported a diminished level of endogenously formed triglycerides and cholesterol from the liver into the blood and a changed lipid composition of lipoproteins of a very low density in the blood. Nutritive value of sunflower seeds in a broiler diet was studied by Selvaraj et al. in 2004. Sunflower seed supplementation of up to 20% did not affect weight gain. Preservation of alpha-tocopherol and subsequent delay in rancidity in sunflower oil by herbs and spices was studied by Beddows et al. Besides describing effects of many other herbs and spices, they reported a beneficial effect of cumin extract and negative effect of cardamom extract upon preservation of alpha-tocopherol and delaying of sunflower seed oil rancidity.

Cardamom is a commonly used flavoring seed especially in eastern cuisine. AI-Zuhair et al. reported anti-inflammatory and anti-spasmodic properties of cardamom in animal models. Cardamom extract could inhibit platelet aggregation and lipid peroxidation was reported by Suneetha and Krishnakantha.

A direct comparison of "cholesterol-lowering" foods (soy-protein, almonds, viscous fibers from oats, barley, psyllium and the vegetables okra and eggplant) with a statin (lovastatin) was reported by Jenkins et al. in 2005. Mixed results were noted: LDL concentration decreased in both diets, with or without statin, and the absolute difference was greater with statin.

Aside from natural products, many pharmacological agents, such as statins, are available for correction of certain lipid abnormalities. However, these agents may have significant side effects. For example, a widely used statin, atorvastatin (Lipitor), may cause myopathy, liver toxicity, pancreatitis, myalgia/arthralgias and many other untoward effects. Many individuals cannot or hesitate to take those medications because of their potential side effects. Many of them look for a "natural" way to manage their lipids.

As stated, statins are a class of drugs used to lower blood cholesterol. They work in the liver to block a substance needed to make cholesterol. They may also help the body reabsorb cholesterol that has accumulated in plaques on the artery walls. This helps prevent further blockage in the blood vessels. Long-term use of statins may reduce existing blockage in narrowed blood vessels. In some people, statins have reduced the risk of heart attack and stroke. However, like all medications, statins have potential side effects. The most common side effects include nausea, diarrhea, constipation, and muscle ache. In addition, two potentially serious side effects are:

1. Elevated liver enzymes. Occasionally, statin use causes an increase in liver enzymes. If the increase is only mild, a individual can continue to take the drug. However, if the increase is severe, a individual may need to stop taking it, which usually reverses the problem. Additionally, certain other cholesterol-lowering drugs, such as gemfibrozil (Lopid) and niacin, increase the risk of liver problems in people who take statins. Because liver problems may develop without symptoms, people who take statins should have their liver function tested periodically.

2. Statin myopathy. Statins may cause muscle pain and tenderness (statin myopathy). In severe cases, muscle cells can break down (rhabdomyolysis) and release a protein called myoglobin into the bloodstream. Myoglobin can impair kidney function and lead to kidney failure. Certain drugs when taken with statins can increase the risk of rhabdomyolysis. These include gemfibrozil, erythromycin (Erythrocin), anti-fungal medications, nefazodone (Serzone), cyclosporine and niacin.

Individuals are instructed to avoid taking statins with grapefruit juice, which alters the body's metabolism of these drugs. Also, doctors generally recommend that people take statins late in the day because the body makes most of its cholesterol at night. Thus, the use of statins is difficult and risky.

An alternative approach to the problem of high cholesterol levels has been the use of ancient, cultural remedies, for example red yeast rice which has been used by the Chinese for many centuries as a food preservative, food colorant and for medicinal purposes to improve circulation and alleviate indigestion. Recently, Chinese and American scientists have developed red yeast rice as a product to lower blood lipids, including cholesterol and triglycerides.

Scientists at Pharmanex and the UCLA Center for Human Nutrition analyzed the properties of Cholestin™. The composition by weight is starch (73%), protein (5.8%) moisture (3-6%), unsaturated fatty acids (1.5%), monacolins (0.4%), ash (3%), and trace amounts of calcium, iron, magnesium, and copper. There are no additives, preservatives, heavy metals, or toxic substances, such as citrinic acid.

In 1977, Professor Endo in Japan discovered a natural cholesterol-lowering substance that is produced by a strain of Monascus yeast. This substance inhibits HMG-CoA reductase, an enzyme that is important for the production of cholesterol in the body. Professor Endo named this substance moncacolin K. Since then, scientists have discovered a total of 8 monacolin-like substances that have cholesterol-lowering properties.

Monacolin K is lovastatin, the active ingredient in the popular statin drug, Mevacor™, which is used for lowering cholesterol. Lovastatin also is believed to be the main cholesterol-lowering ingredient in HypoCol™ and Cholestin™. The lovastatin in Mevacor™ is highly purified and concentrated, while the ingredients in Cholestin™ and HypoCol™ are not. Thus, they contain much lower concentrations of lovastatin than Mevacor™. For example, each 600-mg capsule of Cholestin™ contains less than 2.4 mg of lovastatin whereas tablets of Mevacor™ contain 10 mg or more of this ingredient.

Because none of the components are purified and concentrated, HypoCol™ and Cholestin™ contain a mixture of the 8 yeast-produced monacolins, unsaturated fatty acids, and certain anti-oxidants. Some scientists believe that these other monacolins, unsaturated fatty acids, and anti-oxidants may work together favorably with lovastatin to enhance its cholesterol-lowering effects, as well as its ability in lowering triglycerides and increasing HDL cholesterol. (HDL is considered the "good" form of cholesterol since high levels of HDL cholesterol protect against heart attacks). Further studies in animals and humans will be necessary to test these beliefs.

Chinese scientists conducted most of the animal and human studies on this issue, using either Zhitai or Xuezhikang. The results of some 17 studies involving approximately 900 Chinese subjects with modestly elevated cholesterol levels have been published. In 8 of these studies, there was a control group that received a placebo (a pill with no active ingredients) for comparison purposes. In 9 of the studies, there was no placebo control group. These studies consistently showed that Zhitai and Xuezhikang lower total cholesterol (by an average of 10-30%), lower LDL cholesterol (by an average of 10-20%), lower triglycerides (by an average of 15-25%), and increase HDL (by an average of 7-15%).

Based on the above discussion, diets comprised of cholesterol lowering foods have provided mixed results. Additionally, there is a need for safer agents that individuals could confidently take to correct lipid abnormalities without the risk of significant side effects. There is a need for an easy to obtain, easily digestible, tasty, natural alternative. The present invention addresses this need.

SUMMARY OF THE INVENTION

The above-described disadvantages are greatly overcome or eliminated by the present invention. Besides the individual nuts and oil seeds, at this time there is no scientifically tested combined oil seeds and nuts based natural product formulation that an individual can take as a dietary supplement to correct cholesterol levels. The present invention is a specially formulated blend of oil seeds and nuts chosen due to the individual properties of each. Special cooking techniques are used to preserve the natural nutritive value of each and to enhance their flavor. If taken regularly, the combination assists in controlling the risk factors associated with heart disease and stroke by correcting cholesterol level abnormalities. The combination provides a viable alternative to available drugs, and, as a natural product, it has no known side effects, except to those individuals who are allergic to the particular oil seeds and/or nuts used in the formulation of the novel composition. The present inventive composition may be especially useful for individuals who are either allergic or intolerant to standard drugs. It is intended that any other advantages or objects of the present invention that become apparent or obvious from the detailed description or illustrations contained herein are within the scope of the present invention.

DETAILED DESCRIPTION OF THE INVENTION

Exploiting the known beneficial effects of many individual oil seeds and nuts, the composition of the present invention has been developed. As used herein and throughout, "oil seeds" are those seeds which yield oil, which is edible by humans, when pressed. Additionally, as used herein and throughout, "nuts" comprise a fruit having a kernel, which comprises one or two seeds, within a hardened shell wall. Compared to ordinary fruits, where the seeds can be removed from the flesh, nuts have a compound ovary where the seeds and fruit are fused together.

This specially formulated blend of oil seeds and nuts is manufactured based upon the individual properties of the specific oil seeds and nuts. Additionally, special cooking techniques are described herein to preserve the natural nutritive value and enhance the flavor of the inventive supplement. The composition of the present invention, when properly prepared, assists in the control of certain risk factors for heart disease and stroke by correcting lipid level abnormalities. Additionally, the supplement of the present invention provides users with an alternate or an additional choice, a natural product, to available drugs. Additionally, it is especially useful for individuals who are allergic or otherwise intolerant to standard drugs.

In achieving the health benefits associated with the use of the present composition, it is important to the present invention that not only the oil from the oil seeds and nuts be utilized in the composition, but also the fiber found in these ingredients, as well as other naturally occurring components which are inherent in the selected seeds and nuts. Accordingly, the entire oil seed and nut (with the exception of the non-edible shells of the nuts) are preferably utilized in formulating the present composition.

The composition of the present invention comprises a variety of oil seeds and nuts having therapeutic properties, wherein, in combination, the oil seeds and nuts reduce serum cholesterol levels, thereby reducing a risk factor for heart disease. The composition may further comprise parasite inhibitors, such as, pumpkin seeds, to reduce the likelihood of any possible infection associated with use of the present composition. The composition may further comprise flavor enhancing additives, such as, for example, salt, brown sugar, and the like.

Depending on the types of nuts and oil seeds used, in an exemplary embodiment, the composition comprises nuts in an amount of up to about ⅓ of the total weight of the composition, and oil seeds in an amount of up to about ⅔ of the total weight of the composition. When used, the flavor enhancing additives comprise up to about 2 weight percent ("wt %") based on the total weight of the composition.

In an exemplary embodiment, the types of nuts include at least one of walnuts, almonds, Brazil nuts, cashews, hazelnuts, macadamias, pecans, pine nuts, pistachios, and the like, and combinations comprising at least one of the foregoing. Furthermore in an exemplary embodiment, the oil seeds include at least one of golden flaxseed, brown flaxseed, sunflower seeds, safflower, sesame seeds, poppy seeds, pumpkin seeds, cardamom, fennel seeds, peanuts, and the like, and combinations comprising at least one of the foregoing.

The composition of the present invention is manufactured by heating the individual components, categorizing the individual components into distinct sets, grinding each set into a meal, combining the mealed sets into a single composition, and storing the composition, preferably in a sealed container.

Heat is used for purposes of pasteurization, which assists in destroying harmful microorganisms, and to denature the seeds' germinal center. Denaturing the seeds' germinal center prevents sprouting, which can significantly change the chemical consistency of the seeds or hasten rancidity.

Additionally, appropriate heating enhances the flavor, edibility, and digestibility of the nuts and oil seeds without destroying their positive health effects. However, when the seeds and nuts are heat treated, which, in particular, helps to make flaxseeds, almonds, and sunflower seeds more easily digestible, the heating process can destroy important vitamins and minerals which are required for the proper digestion of the seeds and nuts, and which have certain health benefits. Accordingly, additional types of seeds and nuts, for example, the sesame seeds and poppy seeds, may be added for the purpose of supplementing important vitamins and minerals which are otherwise lost during the heat process.

The individual types of oil seeds and nuts are categorized into sets in order to achieve the proper consistency of the particular type of oil seed and nut so as to enhance digestibility and to maximize the healthful effects of the composition. That is, the digestibility of the oil seeds and nuts depends upon reaching a proper consistency for the particular type of oil seed and nut. Therefore, the types of oil seeds and nuts are categorized into sets based upon the hardiness of the type of oil seed's and nut's skin and body so that the individual set can be ground to the proper consistency to maximize digestibility. Accordingly, the distinct sets are created based upon the hardiness of the type of oil seed's and nut's skin and body and certain specific required features. In this manner, then, each component within the set can be ground to a similar consistency as the other components in the set, wherein such consistency aids in the overall digestibility of the composition.

For example, sesame seeds and poppy seeds have a relatively thin skin compared to almonds. Sunflower seeds and pumpkin seeds, however, have a relatively harder skin compared to almonds, and flaxseeds have a harder skin as compared to sunflower seeds and pumpkin seeds. This difference in degrees of harness of the skin, is part of the reason that sesame seeds require minimal processing, cooking and grinding, as compared to almonds or flaxseeds.

As the edibility, digestibility, and metabolism of an oil seed and nut type is affected by the granularity of the final product, once categorized and separated into their proper sets, each set is ground or milled to achieve a certain granular pattern having a consistency with the following properties: the set is slowly absorbed in the gut once ingested, the consistency improves the overall palatability of the set, and the consistency maximizes the metabolism of the individual components in the set. Slow passage in the gut helps to delay absorption of fats and carbohydrates, and, thus, assists in decreasing the overall fat intake. Another benefit of a relatively slow passage of the set in the gut is that the relatively 'good' fat in the oil seeds and nuts competes and prevents absorption of unhealthy fat from other sources. Therefore, the slower the passage through the gut, the less amount of unhealthy fat from other sources is absorbed by the gut. Additionally, in terms of palatability, it is preferred that the set not be ground to a powder form, as a more granular consistency tends to be more palatable as compared to a more powdered consistency. Furthermore, the metabolism of certain of the types of oil seeds and/or nuts is enhanced by maintaining the type of oil seed and/or nut in a more granular consistency as compared to a more powdery consistency.

The amount of time spent in grinding, and the pressure applied in the grinding process to form the granular final product in each set, are variable and are based upon the natural strength of the seed shell. Once the individual sets are ground, the grounded sets are combined with each other to form the composition.

When used, the flavor enhancing additives may be added to the composition after the oil seeds and nuts have been grinded. Alternatively, the flavor enhancing additives may also be added to the sets, based on the grinding properties of the flavor enhancing additives, and then ground with the types of nuts and/or seeds contained in a particular set.

The present invention is further described in the following Examples. However, it is to be understood that the examples are exemplary only and that modifications and alterations, as would be understood by a person of ordinary skill in the art, are contemplated herein.

Example 1

Exemplary Composition

The following table presents an exemplary listing of ingredients used to formulate an exemplary composition of the present invention.

TABLE 1

| Ingredient | Amount (grams) | Heat Treatment |
| --- | --- | --- |
| Flaxseed Brown (*Linum usitatissimum*) | 75.00 | Roasted |
| Flaxseed Golden (*Linum usitatissimum*) | 30.00 | Roasted |
| Sunflower Seeds (*Helianthus annuus*) | 67.50 | Roasted |
| Almonds (*Prunus amygdalmus dulcis* and *amara*) | 67.50 | Roasted |
| Walnuts (*Juglans regia*) | 30.00 | Roasted |
| Sesame Seeds (*Sesamum indicum*) | 07.50 | Roasted |
| Poppy Seed White (*Papaver somniferum*) | 04.00 | Roasted |
| Poppy Seed Black (*Papaver somniferum*) | 03.50 | Roasted |
| Pumpkin Seeds (*Cucurbita pepo*) | 07.50 | Roasted |
| Cardamom (*Elettaria cardamomum*) | 02.00 | Roasted |
| Fennel Seeds (*Foenimulum vulgare*) | 05.00 | Roasted |
| Salt (Sodium chloride) | 01.00 | |
| Brown Sugar | 05.00 | |

The amounts selected take into consideration the caloric content of each of the oil seeds and nuts; the constipating side-effects associated with some of the oil seeds and nuts; e.g., almonds, sesame seeds, poppy seeds, and walnuts; as well, as the fiber content of each of the oil seeds and nuts. The amounts also achieved the desired cholesterol limiting affects.

Example 2

Method of Preparation

An exemplary method for preparing the composition is presented below.

Heating. In the amounts set forth in Table 1, the nuts and oil seeds were individually heated, either by dry or steam heat, to the specific temperature and for a specific time as shown in Table 2.

TABLE 2

| | Temperature (degrees Fahrenheit) | Time (minutes) |
| --- | --- | --- |
| Flaxseed Brown | 250 | 12 |
| Flaxseed Golden | 250 | 12 |
| Sunflower Seeds | 250 | 8 |
| Almonds | 250 | 10 |
| Walnuts | 250 | 8 |
| Sesame Seeds | 250 | 5 |
| Poppy Seeds White | 250 | 4 |
| Poppy Seeds Black | 250 | 4 |
| Pumpkin Seeds | 250 | 6 |
| Fennel Seeds | 250 | 6 |
| Cardamom | 250 | 6 |

Categorizing into Sets and Grinding. After heating, the nuts and oil seeds were divided into three sets as follows:

Set A: Flaxseed brown, flaxseed golden, cardamom and fennel;

Set B: Sunflower seed, pumpkin seed and walnut; and

Set C: Almond, sesame seed, poppy seed black, and poppy seed white.

Accordingly, Set A comprises about 26 wt % of the total weight of the composition, Set B comprises about 32 wt % of the total weight of the composition, and Set C comprises about 42 wt % of the total weight of the composition.

In the amounts set forth in Table 1, brown sugar and salt were also added to Set A as flavor enhancing additives. The sets were determined based on the grinding or milling properties of the particular type of oil seed and nut. Accordingly, those types of oil seeds and nuts which have hardier skins, for example, and which are more difficult to grind or mill, are ground or milled together. Once the sets were established, each set was then grounded into a granular meal.

Mixing and Storing. The three different meals were then combined. The grounded composition was then stored in sealed containers at room temperature. When unopened, the composition can be stored for up to about 1 year at room temperature. When opened, the composition is preferably consumed within about 2-4 months to prevent desiccation of the composition and loss of flavor.

When used as a food supplement, the unique composition and method of formulation, as disclosed herein, provides numerous and unexpected health benefits. In particular, the composition reduces the total amount of human serum cholesterol and LDL and increases HDL levels. More particularly, in a test performed in 20 healthy volunteers with high cholesterol, total human serum cholesterol levels were found to decrease by up to about 10-15%, LDL levels were found to decrease by up to about 10-15%, and HDL levels were found to increase by up to about 20-25% when ingested in an amount of up to about 30 grams per day over the course of two years.

Additionally, the method of manufacturing and the composition is simpler and less expensive as compared to other cholesterol treatments. Furthermore, because the composition comprises all natural ingredients, it is less likely to cause negative side-effects when taken in recommended doses as compared to synthetic compositions currently on the market.

What is claimed is:

1. A composition for reducing total serum cholesterol and low density lipoprotein levels and for increasing high density lipoprotein levels in a human's bloodstream, wherein said composition is prepared by a process comprising:
   a) combining nuts and oil seeds into the following sets:
      1) a first set comprising 75 g flax seeds brown, 30 g flax seeds golden, 2.0 g cardamom and 5.0 g fennel seeds,
      2) a second set comprising 76.50 g sunflower seeds, 7.50 g pumpkin seeds and 30.0 g walnut, and
      3) a third set comprising 67.50 g almond, 7.50 g sesame seeds, 3.50 g poppy seeds black and 4.0 g poppy seeds white;
   b) grinding each set from (1), (2) and (3) to form ground mixtures of each set; and
   c) combining all of the ground mixtures to form a composition, wherein prior to step (a), all of the nuts and oil seeds of sets (1), (2) and (3) are heated.

2. The composition of claim 1, wherein said first set further comprises a flavor enhancing additive, wherein the flavor enhancing additive comprises at least one of sugar and salt.

3. A method for reducing total serum cholesterol and low density lipoprotein levels and increasing high density lipoprotein levels in a human's bloodstream comprising administering, by ingestion, to a human in need thereof, about 30 grams per day of the composition of either claim 1 or claim 2.

4. A method for forming a dietary supplement which reduces total serum cholesterol and low density lipoprotein levels and increases high density lipoprotein levels in a human's bloodstream, wherein the method comprises:
   a) combining nuts and oil seeds into the following sets:
      1) a first set comprising 75 g flax seed brown, 30 g flaxseed golden, 2.0 g cardamom and 5.0 g fennel seeds,
      2) a second set comprising 76.50 g sunflower seed, 7.50 g pumpkin seeds, and 30.0 g walnut, and
      3) a third set comprising 67.50 g almond, 7.50 g sesame seeds, 3.50 g poppy seeds black and 4.0 g poppy seeds white;
   b) grinding each set of (1), (2) and (3) to form ground mixtures of each set; and
   c) combining all of the ground mixtures to form a composition, wherein prior to step (a), all of the nuts and oil seeds of sets (1), (2) and (3) are heated.

5. The method of claim 4 further comprising adding a flavor enhancing additive to the first set, wherein the flavor enhancing additive comprises at least one of sugar and salt.

* * * * *